(12) United States Patent
Lorenz et al.

(10) Patent No.: US 7,885,442 B2
(45) Date of Patent: Feb. 8, 2011

(54) PERFUSION WEIGHTED MRI WITH LOCAL ARTERIAL INPUT FUNCTIONS

(75) Inventors: Cory Lorenz, Wheaton, MD (US); Thomas Benner, Cambridge, MA (US); Gregory Sorensen, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 560 days.

(21) Appl. No.: 11/569,026

(22) PCT Filed: May 13, 2005

(86) PCT No.: PCT/US2005/016648

§ 371 (c)(1),
(2), (4) Date: Mar. 25, 2008

(87) PCT Pub. No.: WO2005/114229

PCT Pub. Date: Dec. 1, 2005

(65) Prior Publication Data

US 2008/0194943 A1 Aug. 14, 2008

Related U.S. Application Data

(60) Provisional application No. 60/571,621, filed on May 14, 2004.

(51) Int. Cl.
*G06K 9/00* (2006.01)

(52) U.S. Cl. .................................... 382/128; 382/131

(58) Field of Classification Search ................. 382/128, 382/131; 600/419

See application file for complete search history.

(56) References Cited

U.S. PATENT DOCUMENTS

| 5,494,655 | A | 2/1996 | Rocklage et al. ........... 424/9.36 |
| 5,509,412 | A | 4/1996 | Bahn ....................... 128/653.2 |
| 6,389,304 | B1* | 5/2002 | Van Den Brink et al. .... 600/419 |
| 7,436,990 | B2* | 10/2008 | Omi et al. ................... 382/128 |

* cited by examiner

*Primary Examiner*—Phuoc Tran
(74) *Attorney, Agent, or Firm*—Quarles & Brady LLP

(57) ABSTRACT

A method for perfusion weighted imaging in which a plurality of local arterial input functions is estimated at each of a plurality of voxels. At least in part of the basis of the local arterial input functions, a cerebral blood flow at a voxel associated with one of the local arterial input functions is estimated.

18 Claims, 2 Drawing Sheets

PERFUSION WEIGHTED MRI WITH LOCAL ARTERIAL INPUT FUNCTIONS

RELATED APPLICATIONS

This application claims the benefit of priority of U.S. Provisional Patent Application Ser. No. 60/571,621, filed on May 14, 2004, the contents of which are incorporated herein by reference in their entirety.

FIELD OF INVENTION

The invention relates to magnetic resonance imaging ("MRI"), and in particular, to perfusion weighted MRI.

BACKGROUND

Perfusion-weighted magnetic resonance imaging is a common imaging technique used in the clinical treatment of patients with brain pathologies such as stroke or cancer. Perfusion-weighted images are obtained by injecting a bolus of gadolinium chelate into a patient's bloodstream and imaging as it passes through the brain. The gadolinium acts as contrast dye due to its T2 and T2* effects, which cause a drop in transverse relaxation time. This signal drop can then be used to calculate the concentration of the dye in a given voxel of brain tissue over time. The resulting concentration-time curves are then used with standard tracer kinetic models to calculate perfusion metrics such as blood volume, blood flow, and mean transit time.

However, solving the tracer kinetic model equations to calculate blood flow requires the deconvolution of an arterial input function from the measured concentration-time curves. Since the arterial input function is not known explicitly, it must be estimated from measured data. In current practice, a trained specialist examines the measured data and selects a single estimate of the arterial input function. This single estimate is used for the entire brain.

The current practice of estimating an arterial input function relies on the assumptions that the contrast agent reaches all parts of the brain at nearly the same time and that the contrast agent does not disperse significantly on its path from the major arteries to the brain tissue. In many cases, these assumptions are incorrect. However, even if the assumptions were correct, the time required to manually select the arterial input function can make the current practice inconvenient or impractical. In an emergency, the extra time spent identifying a suitable arterial input function could spell the difference between saving and losing brain tissue.

SUMMARY

The invention is based on the recognition that a more accurate representation of cerebral blood flow can be obtained by replacing the global arterial input function with a spatially-variable local arterial input function.

In one aspect, the invention includes a method for perfusion weighted imaging in which a plurality of local arterial input functions is estimated at each of a plurality of voxels. At least in part of the basis of the local arterial input functions, a cerebral blood flow at a voxel associated with one of the local arterial input functions is estimated.

In one embodiment, estimating a plurality of local arterial input functions includes selecting a target voxel; defining a search neighborhood corresponding to the target voxel, the search neighborhood including a plurality of neighborhood voxels; and estimating a local arterial input function for the target voxel at least in part on the basis of measurements associated with each of the neighborhood voxels.

The search neighborhood can be defined as a search neighborhood centered on the target voxel. Alternatively, the search neighborhood can be defined as a search cube centered on the target voxel.

In another embodiment of the invention, estimating a local arterial input function includes evaluating a selected property of a concentration measurement associated with a neighborhood voxel; and determining that the selected property satisfies a criterion. The local arterial input function is then estimated at least in part on the basis of that concentration measurement.

Exemplary properties of the concentration measurement that can be evaluated include a peak amplitude, a full-width half maximum, a first moment, and a slope of a line extending between a baseline and the peak amplitude.

In one embodiment of the invention, the inclusion of only those measurements for which the selected properties satisfy a criterion includes assigning, on the basis of values associated with the selected properties, an overall score to each of the neighborhood voxels; ranking the neighborhood voxels on the basis of their corresponding overall scores; and including only a selected number of neighborhood voxels, the selected neighborhood voxels being selected on the basis of their respective ranks.

Additional embodiments of the invention include those in which the included voxels are weighted on the basis of their respective distances to the target voxel; and a local arterial input function is estimated at least in part on the basis of a weighted combination of the included voxels.

In another aspect, this invention features an MRI ("Magnetic Resonance Imaging") system for perfusion weighted imaging. The system include an MRI scanner for collecting MRI data at each of plurality of voxels and a data processing system for controlling the scanner. The data processing system is configured to estimate a plurality of local arterial input functions at each voxel in the plurality of voxels; and, at least in part of the basis of the local arterial input functions, to estimate a cerebral blood flow at a voxel associated with one of the estimated local arterial input functions.

In some embodiments, the data processing system is configured to select a target voxel and to define a search neighborhood that includes neighborhood voxels and, that corresponds to the target voxel, and to estimate a local arterial input function for the target voxel at least in part on the basis of measurements associated with each of the neighborhood voxels. The search neighborhood can be centered on the target voxel. For example, the search neighborhood can be a search cube centered on the target voxel.

Other embodiments include those in which the data processing system is configured to evaluate a selected property of a concentration measurement associated with a neighborhood voxel, to determine that the selected property satisfies a criterion, and to estimate the local arterial input function at least in part or the concentration measurement.

In yet another embodiments, the data processing system is configured to select the property of the concentration measurement from to be a peak amplitude, a full-width half maximum, a first moment, or a slope of a line extending between a baseline and the peak amplitude.

Additional embodiments include those in which the data processing system is configured to estimate the local arterial input function by assigning, on the basis of values associated with the selected properties, an overall score to each of the neighborhood voxels; ranking the neighborhood voxels on the basis of their corresponding overall scores; and including only a selected number of neighborhood voxels, the selected neighborhood voxels being selected on the basis of their respective ranks.

In some embodiments, the data processing system is configured to weight the included voxels on the basis of their respective distances to the target voxel; and to assign a local arterial input function at least in part on the basis of a weighted combination of the included voxels.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

To monitor cerebral blood flow in a subject, one injects a contrast dye (e.g. gadolinium chelate) into the subject. This contrast dye is selected for its conspicuousness in a magnetic resonance image of the brain.

The contrast dye enters the brain through a number of arteries. The cerebral blood flow eventually distributes the dye throughout the brain. By using magnetic resonance imagining to observe spatial and temporal evolution of dye concentration throughout the brain, one can infer the cerebral blood flow that drives the distribution of the dye.

Figure 1:
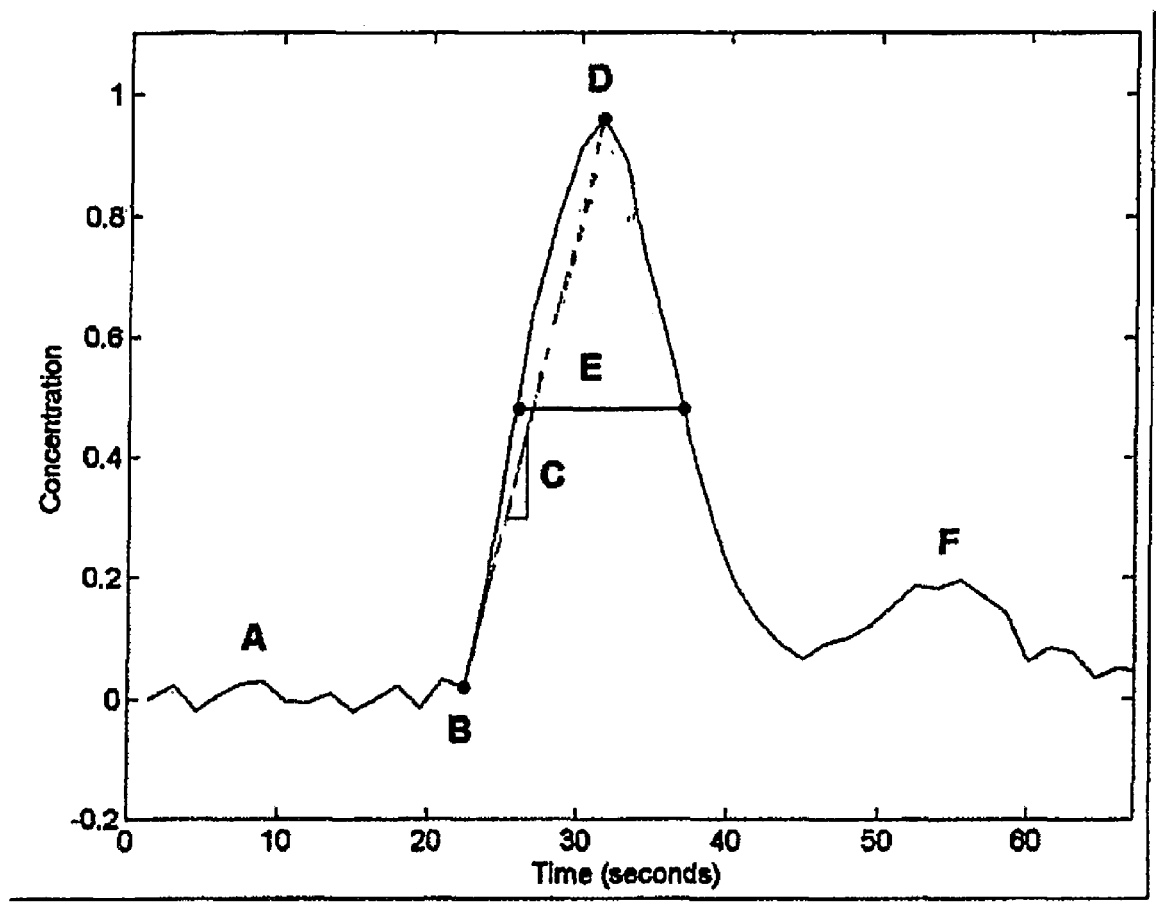
FIG. 1 is a typical arterial input function.

At any voxel in the brain, the concentration of dye entering that voxel, shown in FIG. 1, takes the form of a time-varying function having a rapid rise to an initial narrow peak D, followed by an extended dilution period. The extended dilution period is followed by a second, somewhat broader peak F, which corresponds to the re-circulation of blood containing residual contrast dye back into the voxel. The curve shown in FIG. 1 is referred to as an "arterial input function."

The concentration of dye in a particular voxel depends on the temporal convolution of the arterial input function at that voxel and a residency function, also evaluated at that voxel. As noted above, the arterial input function describes the rate at which the contrast dye enters the voxel. The residency function describes how long the contrast dye remains in the voxel before dissipating outward. A typical residency function has an initial value of unity that diminishes with time. This is consistent with the notion that a contrast dye in a voxel will gradually diffuse outward in response to a concentration gradient.

When multiplied by the cerebral flow rate at a particular voxel, the convolution of the arterial input function at that voxel and the residency function yields the measured concentration of contrast dye at that voxel. Thus, to determine the unknown cerebral flow rate from the measured dye concentration, one must deconvolve the arterial input function from the residency function. This requires knowledge of the arterial input function at that voxel, i.e., the "local" arterial input function.

Figure 2:
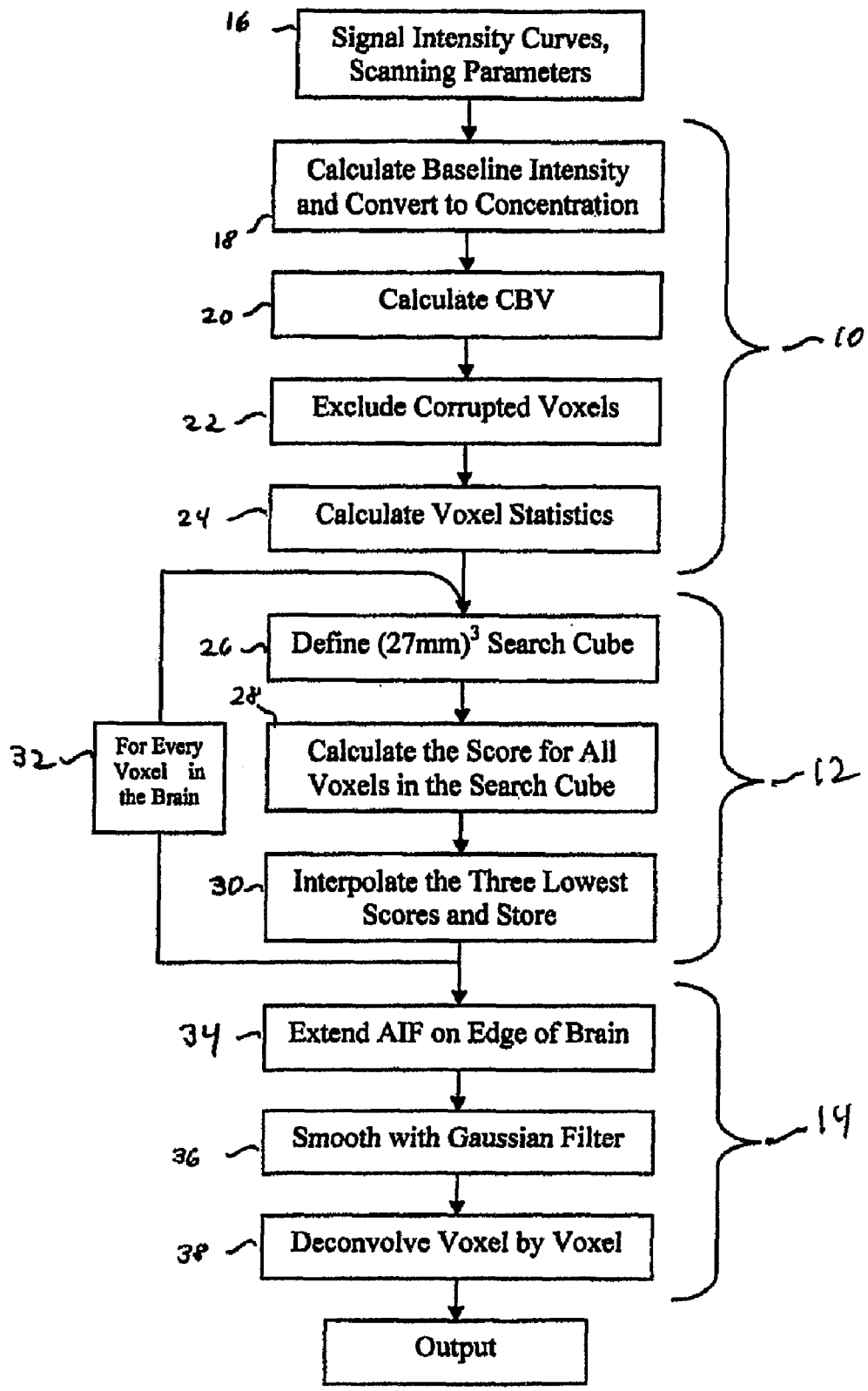
FIG. 2 is a flowchart of a method for estimating local arterial input functions.

Referring to FIG. 2, a method for estimating a local arterial input function can be divided into three stages: a preparatory stage 10, a searching stage 12, and a deconvolution stage 14.

The preparatory stage 10 begins by converting the signal intensity curves into concentration-time curves (steps 16, 18). In doing so, a linear relationship between concentration and the change in transverse relaxation is assumed. A baseline intensity for each voxel is obtained by first finding an average peak time for the whole brain by averaging the time-to-peak for every voxel in the brain. Following that, a baseline intensity is calculated on a voxel-by-voxel basis to be the average of the intensities from time zero to a time that is twelve seconds before the average peak time. The concentration-time curves are then calculated. For each voxel, the cerebral blood volume for that voxel is calculated as the area under the concentration curve for that voxel (step 20).

The next step is to exclude from further consideration those voxels that are clearly unfit for arterial input function selection (step 22). This is done by first excluding voxels having a cerebral blood volume that is either too low (i.e., less than 5% of the maximum cerebral blood volume) or too high (i.e., greater than 60% of the maximum cerebral blood volume). Following this, the first moment of the concentration curve for each voxel is calculated (step 24) and a 30 second arrival window centered on the average peak time is defined. The remaining voxels are inspected to exclude voxels corrupted by noise, vessel pulsation, patient motion, susceptibility artifacts or other sources of artificial signal drops. In particular, a voxel is excluded if the measured concentration of dye entering that voxel has one or more of the following properties:

A first moment that is more than 7.5 seconds before the average peak time. (Because having a majority of the concentration before the expected arrival of the bolus of dye is indicative of noise.)

A maximum value outside of the arrival window. (Because having maximum values well before or after the expected bolus arrival time is indicative of artificial signal drops.)

Two points at 60% of the maximum value separated by more than 26 seconds. (Because a 26 second interval has been found to be long enough for bolus passage.)

A "negative concentration" with an absolute value more than half of its maximum. (Since noise is usually distributed evenly around zero, this will exclude noisy voxels.)

An occurrence, before the arrival window, of a negative concentration change that is greater than 40% of the maximum concentration change. (A large negative concentration change is expected only after the bolus arrives.)

An occurrence, after the arrival window, of a positive concentration change that is greater than 60% of the maximum concentration charge. (A large positive concentration change is expected only when the bolus arrives.)

A mean concentration after the arrival window that is less than two standard deviations above the mean concentration before the arrival window. (Valid arterial input functions have a re-circulation artifact that will increase the post-bolus mean concentration.)

For each of the remaining voxels (hereafter referred as "target" voxels), one then defines a search cube of neighboring voxels centered on a target voxel (step 26). The measured concentration function at each of the neighboring voxels is then evaluated on the basis of how likely it is that that concentration function corresponds to an arterial input function.

In particular, a concentration function for a neighboring voxel is assigned a score on the basis of certain properties. Referring back to FIG. 1, these properties include the amplitude of the first peak D, the first moment of the concentration function, the width of the peak E, and the slope C of a line connecting the peak to the beginning of the rise in concentration B. The four properties noted above are then combined into a single scalar score associated with that neighboring voxel (step 28). The three highest-scoring neighboring voxels are then identified.

Each of these four properties is normalized to fall between 0 and 1. This is done by subtracting out the minimum value of each property in the search cube followed by dividing by the maximum value of each property in the search cube. The score "S" for each of the neighboring voxels in the search cube is given by $$S = FM + FWHM - PV - AS$$

where FM is the first moment, FWHM (which stands for "full width half max") is the width of the first peak at the point at which it has reached its maximum value, PV is the peak value, and AS is the slope of the line extending between the peak value and the baseline of the peak. A low value of FM is indicative of minimal delay. A low value of FWHM, together with high values of PV and AS is indicative of minimal dispersion. The score S falls between −2 and 2, with the best voxels having the lowest scores.

Referring back to FIG. 2, the three lowest-scoring voxels are then weighted on the basis of their location relative to the target voxel (step 30). In particular, the closer a neighboring voxel is to the target voxel, the higher will be the weight associated with that voxel. This is done by interpolating the three best voxels with a 3-D 27 mm FWHM Gaussian kernel. This result is stored as the arterial input function for the target voxel centered in the search cube. The foregoing procedure is then repeated for additional target voxels (step 32) until all voxels in the brain have been processed as described above.

To prevent a bias on the edges of the brain, the arterial input functions are extended out by 14 mm in all directions at the brain periphery, thereby avoiding edge effects during the smoothing process (step 34). This is accomplished by adding extra slices above and below the brain, as well as by using morphological operators to replicate the values on the edge of the brain out an extra 14 mm. The final deconvolution stage begins by smoothing the local arterial input functions (for continuity) with the same 3-D Gaussian kernel used for interpolation (step 36). Finally, the local arterial input functions are deconvolved from the concentration curves (step 38). The deconvolution is carried out by singular value decomposition on a voxel-by-voxel basis.

Exemplary code for implementing the foregoing method using MATLAB™ is given in Appendix A.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Having described the invention, and a preferred embodiment thereof, what is claimed as new, and secured by Letters Patent is:

1. A method for perfusion weighted imaging, the method comprising:
    estimating a plurality of local arterial input functions at each of a plurality of voxels; and
    at least in part on the basis of the local arterial input functions, estimating a cerebral blood flow at a voxel associated with one of the estimated local arterial input functions.

2. The method of claim 1, wherein estimating a plurality of local arterial input functions comprises:
    selecting a target voxel;
    defining a search neighborhood corresponding to the target voxel, the search neighborhood including a plurality of neighborhood voxels; and
    estimating a local arterial input function for the target voxel at least in part on the basis of measurements associated with each of the neighborhood voxels.

3. The method of claim 2, wherein defining a search neighborhood comprises defining a search neighborhood centered on the target voxel.

4. The method of claim 2, wherein defining a search neighborhood comprises defining a search cube centered on the target voxel.

5. The method of claim 2, wherein estimating a local arterial input function comprises:
    evaluating a selected property of a concentration measurement associated with a neighborhood voxel;
    determining that the selected property satisfies a criterion; and
    estimating the local arterial input function at least in part on the basis of the concentration measurement.

6. The method of claim 5, further comprising selecting the property of the concentration measurement from the group consisting of: a peak amplitude, a full-width half maximum, a first moment, and a slope of a line extending between a baseline and the peak amplitude.

7. The method of claim 5, wherein estimating the local arterial input function comprises:
    assigning, on the basis of values associated with the selected properties, an overall score to each of the neighborhood voxels;
    ranking the neighborhood voxels on the basis of their corresponding overall scores; and
    including only a selected number of neighborhood voxels, the selected neighborhood voxels being selected on the basis of their respective ranks.

8. The method of claim 7, further comprising:
    weighting the included voxels on the basis of their respective distances to the target voxel; and
    estimating a local arterial input function at least in part on the basis of a weighted combination of the included voxels.

9. A computer-readable storage medium having encoded thereon instructions that, when executed by a computer processor, cause the computer processor to:
    estimate a plurality of local arterial input functions at each of a plurality of voxels; and
    at least in part on the basis of the local arterial input functions, estimate a cerebral blood flow at a voxel associated with one of the estimated local arterial input functions.

10. An MRI system for perfusion weighted imaging, the system comprising:
    an MRI scanner for collecting MRI data at each of plurality of voxels; and
    a data processing system for controlling the scanner, the data processing system being configured to estimate a plurality of local arterial input functions at each voxel in the plurality of voxels; and at least in part of the basis of the local arterial input functions, to estimate a cerebral blood flow at a voxel associated with one of the estimated local arterial input functions.

11. The system of claim 10, wherein the data processing system is configured:
   to select a target voxel;
   to define a search neighborhood corresponding to the target voxel, the search neighborhood including a plurality of neighborhood voxels; and
   to estimate a local arterial input function for the target voxel at least in part on the basis of measurements associated with each of the neighborhood voxels.

12. The system of claim 11, wherein the data processing system is configured to define a search neighborhood centered on the target voxel.

13. The system of claim 11, wherein the data processing system is configured to define a search cube centered on the target voxel.

14. The system of claim 11, wherein the data processing system is configured:
   to evaluate a selected property of a concentration measurement associated with a neighborhood voxel;
   to determine that the selected property satisfies a criterion; and
   to estimate the local arterial input function at least in part on the basis of the concentration measurement.

15. The system of claim 14, wherein the data processing system is configured to select the property of the concentration measurement from the group consisting of a peak amplitude, a full-width half maximum, a first moment, and a slope of a line extending between a baseline and the peak amplitude.

16. The system of claim 14, wherein the data processing system is configured to estimate the local arterial input function by:
   assigning, on the basis of values associated with the selected properties, an overall score to each of the neighborhood voxels;
   ranking the neighborhood voxels on the basis of their corresponding overall scores; and
   including only a selected number of neighborhood voxels, the selected neighborhood voxels being selected on the basis of their respective ranks.

17. The system of claim 16, wherein the data processing system is configured:
   to weight the included voxels on the basis of their respective distances to the target voxel; and
   to assign a local arterial input function at least in part on the basis of a weighted combination of the included voxels.

18. The system of claim 10, further comprising a computer-readable medium having encoded thereon instructions that, when executed, cause the data processing system to execute the method recited in claim 1.

* * * * *